United States Patent [19]

de Wied

[11] Patent Number: 4,593,017

[45] Date of Patent: Jun. 3, 1986

[54] METHODS OF TREATING PATIENTS USING A PHARMACEUTICAL PREPARATION CONTAINING AN α-ENDORFINE FRAGMENT

[75] Inventor: David de Wied, Bilthoven, Netherlands

[73] Assignee: Akzo N.V., Arnhem, Netherlands

[21] Appl. No.: 504,276

[22] Filed: Jun. 14, 1983

[30] Foreign Application Priority Data

Jun. 14, 1982 [NL] Netherlands ................. 8202403

[51] Int. Cl.[4] ............... A61K 37/00; A61K 49/00; G01N 31/00; G01N 33/48
[52] U.S. Cl. ........................... 514/16; 424/9; 530/302; 530/328
[58] Field of Search ............... 424/177, 9; 260/112.5 E, 112.5 R; 514/2, 16

[56] References Cited

U.S. PATENT DOCUMENTS 4,139,504  2/1979  Coy ................... 424/177 X

FOREIGN PATENT DOCUMENTS 0004394 10/1979 European Pat. Off. .

OTHER PUBLICATIONS van Nispen, J. W. et al, *Pharmac. Ther.*, vol. 16, 1982, pp. 67–102.
Miller, R. J. et al., (Dept. Pharmacol. & Phys. Sci., Univ. of Chicago, Chicago, Ill.), "Enkephalins and Endorphins", Academic Press, pp. 297–303, 348–363, 372–375.

*Primary Examiner*—Robert J. Warden
*Assistant Examiner*—Jeremy Jay
*Attorney, Agent, or Firm*—Abelman Frayne Rezac & Schwab

[57] ABSTRACT

The invention relates to the use of (2-9)-α-endorfine for dopaminergic and vasopressin-releasing properties.

3 Claims, No Drawings

METHODS OF TREATING PATIENTS USING A PHARMACEUTICAL PREPARATION CONTAINING AN α-ENDORFINE FRAGMENT

The invention relates to the pharmaceutical use of a particular fragment of the peptide α-endorfine.

α- and γ-endorfines are fragments of β-endorfine. α-, β- and γ-endorfine have been tested in a large number of test systems, such as analgesic test systems and behavioral test systems.

In a number of behavioral test systems, α-endorfines and γ-endorfines are found to display an opposite effect. A cautious conclusion from the test results was that α-endorfine would possess psychostimulating activity and γ-endorfine neuroleptic activity.

The removal of the first aminoacid (Tyr) from γ-endorfine, resulting in des-Tyr-γ-endorfine, turned out to produce a strengthening of the neuroleptic properties and a virtual disappearance of the opiate properties (see European Patent Application No. 0,004,394).

Further structure activity studies in respect of γ-endorfine derivatives led to the conclusion that the smallest peptide, which still possesses all neuroleptic properties, is the C-terminal fragment 6-17 of γ-endorfine (see European Patent Application No. 0,015,036).

Structure activity studies in respect of α-endorfine derivatives have hitherto been given far less attention.

α-Endorfine is, as just stated, known as a psychostimulant. It is also known that on C-terminal cleavage these psychostimulant properties as yet remain preserved.

D. H. Coy, in a large series of U.S. patents (see, for example, U.S. Pat. No. 4,127,517 to U.S. Pat. No. 4,127,541) describes that successive C-terminal cleavage of a β-endorfine derivative, wherein the second aminoacid is replaced by a D-aminoacid, in each case leads to peptides having psychostimulant properties, but also sedative, hypnotic, analgesic and prolactine-releasing properties.

It has further been found (see e.g. Pharmac. Ther. 16, 67, 1982) that the α-endorfine fragment (2-9)-α-endorfine is 10 times less active than α-endorfine in the well-known pole-jumping test. In other words, (2-9)-α-endorfine is markedly weaker in delaying the extinction of conditioned avoidance behavior than α-endorfine. Based on this test result it may be concluded that this peptide does not possess any practically useful psychostimulant action.

Surprisingly, it has now been found that the fragment (2-9)-α-endorfine and structurally very closely related analogues thereof, having an aminoacid sequence:

H-R(1)-Gly-L-Phe-R(2)-L-Thr-L-Ser-L-Glu-L-Lys-OH, I wherein R(1) represents Gly or L-Ala, and R(2) represents L-Met, L-Met(O) or L-Met(O₂), as well as the functional derivatives thereof, possess particularly valuable dopaminergic properties, as a result of which they are suitable for use in the treatment of Parkinson's disease, and that they moreover stimulate the endogenous production of vasopressin, as a result of which they are useful in all treatments wherein hitherto the hormone vasopressin has been prescribed.

The latter use whereby the endogenous vasopressin production is stimulated, has the additional advantage that the side effects which accompany the administration of exogenous vasopressin—e.g. the effect on blood pressure—are much less pronounced.

Through its stimulation of endogenous vasopressin release, the peptide of formula I and derivatives thereof may be used as an anti-diuretic agent or vasoconstrictive agent, so treating patients suffering from for example diabetis insipidus or bleeding oesophageal varices, but may also be used in the treatment of patients suffering from cognitive disabilities such as amnesic syndromes.

As a further consequence of the latter utility (vasopressin release) the peptide of formula I or its functional derivative may obviously be used as a diagnostic aid for detecting subjects with deficient production of vasopressin.

Functional derivatives are:
(a) the C-terminal lower aliphatic esters (1-6 C atoms), such as the methyl, ethyl, propyl, isopropyl, butyl or isobutyl ester,
(b) C-terminal amides or monomethyl- or dimethyl-substituted amides and
(c) pharmaceutically acceptable salts including acid addition salts.

The peptides according to the formula I described above are prepared in the usual manner for peptides, via fragment condensation or via the solid phase technique.

The use of the peptide:

H-Gly-Gly-L-Phe-L-Met-L-Thr-L-Ser-L-Glu-L-Lys-OH and of pharmaceutically acceptable acid addition salts thereof is preferred.

The peptides of the formula I are preferably administered parenterally, rectally or intranasally (via a nasal spray). They can be mixed, in the conventional manner, with conventional pharmaceutical carriers (fillers, solvents, diluents etc.).

The dosage in which the peptides according to the invention are preferably administered varies between 0.1 μg and 10 mg per kg of body weight per day. The preferred daily dosage range for administration to human beings is from 5 μg to 500 mg.

Vasopressin release

The effect of (2-9)-α-endorfine on AVP (arg-vasopressin) levels of eye plexus plasma was tested.

Female Wistar rats (140-160 g) were anaesthetized with ether for a strictly controlled period of 45 seconds. Samples of eye plexus blood were taken and stored in cooled plastic tubes to which heparin was added. The tubes were centrifuged at 4° C. in order to obtain the plasma. The immunoreactive AVP was directly measured in 20 μl of eye plexus plasma with the aid of RIA (radio-immuno-assay) methods.

The rats were treated with placebo or with 10 μg of (2-9)-α-endorfine per rat, injected subcutaneously.

| Period after injection, in minutes | AVP levels expressed in pg/ml | |
|---|---|---|
| | placebo (0.5 ml of saline solution) | (2-9)-α-endorfine |
| 2 | <50 | 667 |
| 5 | <50 | 92 |
| 10 | <50 | 78 |

Apomorphine induced stereotyped sniffing

Subcutaneous treatment of rats with apomorphine (250 μg/kg) elicits hyperlocomotion and especially stereotyped sniffing behavoir. Increase of this stereotyped sniffing by pretreatment with the drug to be tested in considered to be an indication for dopaminergic activity.

Groups of rats were subcutaneously injected with placebo (0.5 ml saline), (2–9)-α-endorfine (50 μg) or (3–9)-α-endorfine (50 μg) and after 1 h. with apomorphine (250 μg/kg). An additional group of rats received two placebo (0.5 ml saline) injections. Twenty minutes after the last injection the rats were tested in a small open field and the duration of stereotyped sniffing was measured for 4 min.

| Treatment | Results (Stereotyped) sniffing sec. | | Number of rats |
|---|---|---|---|
| placebo | placebo | 30.7 | (5) |
| placebo | apomorphine | 121.4 | (6) |
| (2–9)-α-endorfine | apomorphine | 158.0 | (6) |
| (3–9)-α-endorfine | apomorphine | 115.3 | (6) |

Apomorphine (250 μg/kg, s.c.) induces stereotyped sniffing and this response is potentiated by pretreatment with 50 μg (2–9)-α-endorfine; pretreatment with (3–9)-α-endorfine does not potentiate the effect of apomorphine.

EXAMPLE

Injection preparation

A freeze-dried mixture in a sealed ampoule consisted of 0.5 mg of H-Gly-Gly-L-Phe-L-Met-L-Thr-L-Ser-L-Glu-L-Lys-OH and 50 mg of mannitol.

Before injection, 1 ml of water was added to the mixture in the ampoule.

I claim:

1. Method for stimulating endogenous vasopressin release in patients which comprises administering a vasopressin-releasing effective amount of a peptide having the formula I:

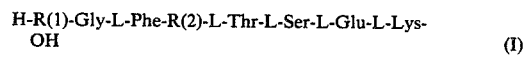

$$\text{H-R(1)-Gly-L-Phe-R(2)-L-Thr-L-Ser-L-Glu-L-Lys-OH} \quad (I)$$

wherein R(1) represents Gly or L-Ala and R(2) represents L-Met, L-Met(O) or L-Met(O$_2$), a physiologically acceptable or C-terminal C$_1$–C$_6$ aliphatic ester or a C-terminal unsubstituted mono- or di-methyl amide thereof, together with one or more pharmaceutically acceptable carriers.

2. Method for the treatment of patients suffering from cognitive disabilities, comprising administering to said patients an effective amount for such treatment of the peptide of formula I and its derivatives as defined in claim 1 in admixture with a pharmaceutically acceptable carrier.

3. Method for the treatment of patients in need for an antidiuretic agent comprising administering to said patients an antidiuretically effective amount of the peptide of formula I and its derivatives as defined in claim 1 in admixture with a pharmaceutically acceptable carrier.

* * * * *